(12) United States Patent
Ryan

(10) Patent No.: US 8,506,620 B2
(45) Date of Patent: Aug. 13, 2013

(54) PROSTHETIC CARDIAC AND VENOUS VALVES

(75) Inventor: Timothy R. Ryan, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 261 days.

(21) Appl. No.: 12/617,850

(22) Filed: Nov. 13, 2009

(65) Prior Publication Data

US 2010/0057194 A1 Mar. 4, 2010

Related U.S. Application Data

(62) Division of application No. 11/527,769, filed on Sep. 26, 2006, now abandoned.

(60) Provisional application No. 60/720,398, filed on Sep. 26, 2005.

(51) Int. Cl.
*A61F 2/24* (2006.01)

(52) U.S. Cl.
USPC .......................................... 623/1.24; 623/2.12

(58) Field of Classification Search
None
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos |
| 4,339,831 A | 7/1982 | Johnson |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,647,283 A | 3/1987 | Carpentier et al. |
| 4,648,881 A | 3/1987 | Carpentier et al. |
| 4,662,885 A | 5/1987 | DiPisa, Jr. |
| 4,665,906 A | 5/1987 | Jervis |

(Continued)

FOREIGN PATENT DOCUMENTS

| | | |
|---|---|---|
| CN | 2007-100074433 | 1/2007 |
| DE | 195 32 846 | 3/1997 |

(Continued)

OTHER PUBLICATIONS

U.S. Appl. No. 61/192,199, filed Sep. 15, 2008.

(Continued)

*Primary Examiner* — Thomas J Sweet
*Assistant Examiner* — Rebecca Preston

(57) ABSTRACT

A prosthetic heart or venous valve, the valve including a central tissue structure with multiple tissue lobes extending from a common central area, wherein each of the lobes includes a longitudinal slot. The valve further includes a plurality of leaflets, each extending from the central tissue structure and positioned between two adjacent lobes, wherein each of the leaflets has a free end spaced from the central tissue structure, and also has a compressible and expandable stent frame with a plurality of extending arms, wherein each of the extending arms of the stent frame is positioned at least partially within one of the longitudinal slots of the central tissue structure.

13 Claims, 6 Drawing Sheets

(56) References Cited

U.S. PATENT DOCUMENTS

| | | |
|---|---|---|
| 4,681,908 A | 7/1987 | Broderick et al. |
| 4,710,192 A | 12/1987 | Liotta et al. |
| 4,787,899 A | 11/1988 | Lazarus |
| 4,787,901 A | 11/1988 | Baykut |
| 4,796,629 A | 1/1989 | Grayzel |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,217,483 A | 6/1993 | Tower |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,482,424 A | 1/1996 | Jones et al. |
| 5,489,297 A | 2/1996 | Duran |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 * | 12/2002 | Greenhalgh ................ 623/1.24 |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |

| | | | | | | |
|---|---|---|---|---|---|---|
| 6,569,196 B1 | 5/2003 | Vesely | 7,300,457 B2 | 11/2007 | Palmaz | |
| 6,585,758 B1 | 7/2003 | Chouinard et al. | 7,300,463 B2 | 11/2007 | Liddicoat | |
| 6,592,546 B1 | 7/2003 | Barbut et al. | 7,316,706 B2 | 1/2008 | Bloom et al. | |
| 6,605,112 B1 | 8/2003 | Moll et al. | 7,329,278 B2 | 2/2008 | Seguin | |
| 6,613,077 B2 | 9/2003 | Gilligan et al. | 7,335,218 B2 | 2/2008 | Wilson et al. | |
| 6,622,604 B1 | 9/2003 | Chouinard et al. | 7,338,520 B2 | 3/2008 | Bailey et al. | |
| 6,635,068 B2 | 10/2003 | Dubrul et al. | 7,374,571 B2 | 5/2008 | Pease et al. | |
| 6,652,571 B1 | 11/2003 | White et al. | 7,381,218 B2 | 6/2008 | Schreck | |
| 6,652,578 B2 | 11/2003 | Bailey et al. | 7,384,411 B1 | 6/2008 | Condado | |
| 6,656,213 B2 | 12/2003 | Solem | 7,429,269 B2 | 9/2008 | Schwammenthal et al. | |
| 6,663,663 B2 | 12/2003 | Kim et al. | 7,442,204 B2 | 10/2008 | Schwammenthal et al. | |
| 6,669,724 B2 | 12/2003 | Park et al. | 7,462,191 B2 | 12/2008 | Spenser et al. | |
| 6,673,089 B1 | 1/2004 | Yassour et al. | 7,470,284 B2 | 12/2008 | Lambrecht et al. | |
| 6,673,109 B2 | 1/2004 | Cox | 7,481,838 B2 | 1/2009 | Carpentier et al. | |
| 6,676,698 B2 | 1/2004 | McGuckin, Jr. et al. | 7,544,206 B2 | 6/2009 | Cohn et al. | |
| 6,682,558 B2 | 1/2004 | Tu et al. | 7,556,646 B2 | 7/2009 | Yang et al. | |
| 6,682,559 B2 | 1/2004 | Myers et al. | 7,799,069 B2 * | 9/2010 | Bailey et al. | 623/1.26 |
| 6,685,739 B2 | 2/2004 | DiMatteo et al. | 8,246,675 B2 * | 8/2012 | Zegdi | 623/1.24 |
| 6,689,144 B2 | 2/2004 | Gerberding | 8,308,797 B2 * | 11/2012 | Paniagua et al. | 623/2.14 |
| 6,689,164 B1 | 2/2004 | Seguin | 2001/0001314 A1 | 5/2001 | Davison et al. | |
| 6,692,512 B2 | 2/2004 | Jang | 2001/0002445 A1 | 5/2001 | Vesely | |
| 6,692,513 B2 | 2/2004 | Streeter et al. | 2001/0007956 A1 | 7/2001 | Letac et al. | |
| 6,695,878 B2 | 2/2004 | McGuckin, Jr. et al. | 2001/0010017 A1 | 7/2001 | Letac et al. | |
| 6,702,851 B1 | 3/2004 | Chinn et al. | 2001/0011189 A1 | 8/2001 | Drasler et al. | |
| 6,719,789 B2 | 4/2004 | Cox | 2001/0021872 A1 | 9/2001 | Bailey et al. | |
| 6,730,118 B2 | 5/2004 | Spenser et al. | 2001/0025196 A1 | 9/2001 | Chinn et al. | |
| 6,730,377 B2 | 5/2004 | Wang | 2001/0032013 A1 | 10/2001 | Marton | |
| 6,733,525 B2 | 5/2004 | Yang et al. | 2001/0039450 A1 | 11/2001 | Pavcnik et al. | |
| 6,736,846 B2 | 5/2004 | Cox | 2001/0041928 A1 | 11/2001 | Pavcnik et al. | |
| 6,752,828 B2 | 6/2004 | Thornton | 2001/0044647 A1 | 11/2001 | Pinchuk et al. | |
| 6,758,855 B2 | 7/2004 | Fulton, III et al. | 2002/0010508 A1 | 1/2002 | Chobotov | |
| 6,769,434 B2 | 8/2004 | Liddicoat et al. | 2002/0029014 A1 | 3/2002 | Jayaraman | |
| 6,786,925 B1 | 9/2004 | Schoon et al. | 2002/0032480 A1 | 3/2002 | Spence et al. | |
| 6,790,229 B1 | 9/2004 | Berreklouw | 2002/0032481 A1 | 3/2002 | Gabbay | |
| 6,792,979 B2 | 9/2004 | Konya et al. | 2002/0035396 A1 | 3/2002 | Heath | |
| 6,797,002 B2 | 9/2004 | Spence | 2002/0042650 A1 | 4/2002 | Vardi et al. | |
| 6,821,297 B2 | 11/2004 | Snyders | 2002/0052651 A1 | 5/2002 | Myers et al. | |
| 6,830,575 B2 | 12/2004 | Stenzel et al. | 2002/0058995 A1 | 5/2002 | Stevens | |
| 6,830,584 B1 | 12/2004 | Seguin | 2002/0072789 A1 | 6/2002 | Hackett et al. | |
| 6,830,585 B1 | 12/2004 | Artof | 2002/0099439 A1 | 7/2002 | Schwartz et al. | |
| 6,846,325 B2 | 1/2005 | Liddicoat | 2002/0103533 A1 | 8/2002 | Langberg et al. | |
| 6,866,650 B2 | 3/2005 | Stevens | 2002/0107565 A1 | 8/2002 | Greenhalgh | |
| 6,872,223 B2 | 3/2005 | Roberts | 2002/0111674 A1 | 8/2002 | Chouinard et al. | |
| 6,875,231 B2 | 4/2005 | Anduiza et al. | 2002/0123802 A1 | 9/2002 | Snyders | |
| 6,883,522 B2 | 4/2005 | Spence et al. | 2002/0133183 A1 | 9/2002 | Lentz et al. | |
| 6,887,266 B2 | 5/2005 | Williams et al. | 2002/0138138 A1 | 9/2002 | Yang | |
| 6,890,330 B2 | 5/2005 | Streeter et al. | 2002/0151970 A1 | 10/2002 | Garrison et al. | |
| 6,893,460 B2 | 5/2005 | Spenser et al. | 2002/0161392 A1 | 10/2002 | Dubrul | |
| 6,896,690 B1 | 5/2005 | Lambrecht et al. | 2002/0161394 A1 | 10/2002 | Macoviak et al. | |
| 6,908,481 B2 | 6/2005 | Cribier | 2002/0193871 A1 | 12/2002 | Beyersdorf et al. | |
| 6,913,600 B2 | 7/2005 | Valley et al. | 2003/0014104 A1 | 1/2003 | Cribier | |
| 6,929,653 B2 | 8/2005 | Streeter | 2003/0023300 A1 | 1/2003 | Bailey et al. | |
| 6,936,066 B2 | 8/2005 | Palmaz et al. | 2003/0023303 A1 | 1/2003 | Palmaz et al. | |
| 6,939,365 B1 | 9/2005 | Fogarty et al. | 2003/0028247 A1 | 2/2003 | Cali | |
| 6,951,571 B1 | 10/2005 | Srivastava | 2003/0036791 A1 | 2/2003 | Philipp et al. | |
| 6,986,742 B2 | 1/2006 | Hart et al. | 2003/0040772 A1 | 2/2003 | Hyodoh et al. | |
| 6,989,027 B2 | 1/2006 | Allen et al. | 2003/0040792 A1 | 2/2003 | Gabbay | |
| 6,989,028 B2 | 1/2006 | Lashinski et al. | 2003/0050694 A1 | 3/2003 | Yang et al. | |
| 6,991,649 B2 | 1/2006 | Sievers | 2003/0055495 A1 | 3/2003 | Pease et al. | |
| 7,018,401 B1 | 3/2006 | Hyodoh et al. | 2003/0065386 A1 | 4/2003 | Weadock | |
| 7,018,408 B2 | 3/2006 | Bailey et al. | 2003/0069492 A1 | 4/2003 | Abrams et al. | |
| 7,041,128 B2 | 5/2006 | McGuckin, Jr. et al. | 2003/0109924 A1 | 6/2003 | Cribier | |
| 7,044,966 B2 | 5/2006 | Svanidze et al. | 2003/0125795 A1 | 7/2003 | Pavcnik et al. | |
| 7,048,014 B2 | 5/2006 | Hyodoh et al. | 2003/0130726 A1 | 7/2003 | Thorpe et al. | |
| 7,070,616 B2 * | 7/2006 | Majercak et al. ............ 623/1.24 | 2003/0130729 A1 | 7/2003 | Paniagua et al. | |
| 7,097,659 B2 | 8/2006 | Woolfson et al. | 2003/0139804 A1 | 7/2003 | Hankh et al. | |
| 7,101,396 B2 | 9/2006 | Artof et al. | 2003/0149475 A1 | 8/2003 | Hyodoh et al. | |
| 7,105,016 B2 | 9/2006 | Shiu et al. | 2003/0149476 A1 | 8/2003 | Damm et al. | |
| 7,115,141 B2 | 10/2006 | Menz et al. | 2003/0149478 A1 | 8/2003 | Figulla et al. | |
| 7,147,663 B1 | 12/2006 | Berg et al. | 2003/0153974 A1 | 8/2003 | Spenser et al. | |
| 7,153,324 B2 | 12/2006 | Case et al. | 2003/0181850 A1 | 9/2003 | Diamond et al. | |
| 7,160,319 B2 | 1/2007 | Chouinard et al. | 2003/0191519 A1 | 10/2003 | Lombardi et al. | |
| 7,175,656 B2 | 2/2007 | Khairkhahan | 2003/0199913 A1 | 10/2003 | Dubrul et al. | |
| 7,186,265 B2 | 3/2007 | Sharkawy et al. | 2003/0199963 A1 | 10/2003 | Tower et al. | |
| 7,195,641 B2 | 3/2007 | Palmaz et al. | 2003/0199971 A1 | 10/2003 | Tower et al. | |
| 7,198,646 B2 | 4/2007 | Figulla et al. | 2003/0212410 A1 | 11/2003 | Stenzel et al. | |
| 7,201,761 B2 | 4/2007 | Woolfson et al. | 2003/0212452 A1 | 11/2003 | Zadno-Azizi et al. | |
| 7,201,772 B2 | 4/2007 | Schwammenthal et al. | 2003/0212454 A1 | 11/2003 | Scott et al. | |
| 7,252,682 B2 | 8/2007 | Seguin | 2003/0225445 A1 | 12/2003 | Derus et al. | |

| | | |
|---|---|---|
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Bergheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |

| | | | | | | |
|---|---|---|---|---|---|---|
| 2007/0244557 | A1 | 10/2007 | Rafiee et al. | DE | 100 49 815 | 4/2002 |
| 2007/0250160 | A1 | 10/2007 | Rafiee | EP | 0103546 | 3/1984 |
| 2007/0255394 | A1 | 11/2007 | Ryan | EP | 0 170 262 | 2/1986 |
| 2007/0255396 | A1 | 11/2007 | Douk et al. | EP | 0597967 | 12/1994 |
| 2007/0288000 | A1 | 12/2007 | Bonan | EP | 0850607 | 7/1998 |
| 2008/0004696 | A1 | 1/2008 | Vesely | EP | 1057459 A1 | 6/2000 |
| 2008/0009940 | A1 | 1/2008 | Cribier | EP | 1057460 A1 | 6/2000 |
| 2008/0015671 | A1 | 1/2008 | Bonhoeffer | EP | 1088529 | 4/2001 |
| 2008/0021552 | A1 | 1/2008 | Gabbay | EP | 1255510 | 11/2002 |
| 2008/0048656 | A1 | 2/2008 | Tan | EP | 0937439 B1 | 9/2003 |
| 2008/0065011 | A1 | 3/2008 | Marchand et al. | EP | 1340473 | 9/2003 |
| 2008/0065206 | A1 | 3/2008 | Liddicoat | EP | 0819013 | 6/2004 |
| 2008/0071361 | A1 | 3/2008 | Tuval et al. | FR | 2788217 | 12/1999 |
| 2008/0071362 | A1 | 3/2008 | Tuval et al. | GB | 2056023 | 3/1981 |
| 2008/0071363 | A1 | 3/2008 | Tuval et al. | GB | 2433700 | 12/2007 |
| 2008/0071366 | A1 | 3/2008 | Tuval et al. | SU | 1271508 | 11/1986 |
| 2008/0071368 | A1 | 3/2008 | Tuval et al. | WO | 91/17720 | 11/1991 |
| 2008/0077234 | A1 | 3/2008 | Styrc | WO | 93/01768 | 2/1993 |
| 2008/0082165 | A1 | 4/2008 | Wilson et al. | WO | 95/29640 | 11/1995 |
| 2008/0082166 | A1 | 4/2008 | Styrc et al. | WO | 98/14137 | 4/1998 |
| 2008/0133003 | A1 | 6/2008 | Seguin et al. | WO | 98/29057 | 7/1998 |
| 2008/0140189 | A1 | 6/2008 | Nguyen et al. | WO | 99/33414 | 7/1999 |
| 2008/0147105 | A1 | 6/2008 | Wilson et al. | WO | 00/41652 | 7/2000 |
| 2008/0147180 | A1 | 6/2008 | Ghione et al. | WO | 00/44313 | 8/2000 |
| 2008/0147181 | A1 | 6/2008 | Ghione et al. | WO | 00/47136 | 8/2000 |
| 2008/0147182 | A1 | 6/2008 | Righini et al. | WO | 00/47139 | 8/2000 |
| 2008/0154355 | A1 | 6/2008 | Benichow et al. | WO | 01/35870 | 5/2001 |
| 2008/0154356 | A1 | 6/2008 | Obermiller et al. | WO | 01/49213 | 7/2001 |
| 2008/0161910 | A1 | 7/2008 | Revuelta et al. | WO | 01/54625 | 8/2001 |
| 2008/0161911 | A1 | 7/2008 | Revuelta et al. | WO | 01/62189 | 8/2001 |
| 2008/0183273 | A1 | 7/2008 | Mesana et al. | WO | 01/64137 | 9/2001 |
| 2008/0188928 | A1 | 8/2008 | Salahieh et al. | WO | 01/76510 | 10/2001 |
| 2008/0215143 | A1 | 9/2008 | Seguin et al. | WO | 02/22054 | 3/2002 |
| 2008/0215144 | A1 | 9/2008 | Ryan et al. | WO | 02/36048 | 5/2002 |
| 2008/0228254 | A1 | 9/2008 | Ryan | WO | 02/41789 | 5/2002 |
| 2008/0228263 | A1 | 9/2008 | Ryan | WO | 02/43620 | 6/2002 |
| 2008/0234797 | A1 | 9/2008 | Styrc | WO | 02/47575 | 6/2002 |
| 2008/0243246 | A1 | 10/2008 | Ryan et al. | WO | 02/49540 | 6/2002 |
| 2008/0255651 | A1 | 10/2008 | Dwork | WO | 03/003943 | 1/2003 |
| 2008/0255660 | A1 | 10/2008 | Guyenot et al. | WO | 03/003949 | 1/2003 |
| 2008/0255661 | A1 | 10/2008 | Straubinger et al. | WO | 03/011195 | 2/2003 |
| 2008/0262593 | A1 | 10/2008 | Ryan et al. | WO | 03/030776 | 4/2003 |
| 2008/0269878 | A1 | 10/2008 | Iobbi | WO | WO 03/088809 | 10/2003 |
| 2009/0005863 | A1 | 1/2009 | Goetz et al. | WO | WO 03/092554 | 11/2003 |
| 2009/0012600 | A1 | 1/2009 | Styrc et al. | WO | 2004/019811 | 3/2004 |
| 2009/0048656 | A1 | 2/2009 | Wen | WO | 2004/019825 | 3/2004 |
| 2009/0054976 | A1 | 2/2009 | Tuval et al. | WO | 2004/023980 | 3/2004 |
| 2009/0069886 | A1 | 3/2009 | Suri et al. | WO | 2004/041126 | 5/2004 |
| 2009/0069887 | A1 | 3/2009 | Righini et al. | WO | 2004/058106 | 7/2004 |
| 2009/0069889 | A1 | 3/2009 | Suri et al. | WO | 2004/089250 | 10/2004 |
| 2009/0099653 | A1 | 4/2009 | Suri et al. | WO | 2005/004753 | 1/2005 |
| 2009/0138079 | A1 | 5/2009 | Tuval et al. | WO | 2005/027790 | 3/2005 |
| 2009/0164004 | A1 | 6/2009 | Cohn | WO | 2005/046528 | 5/2005 |
| 2009/0171447 | A1 | 7/2009 | VonSegesser et al. | WO | 2006/026371 | 3/2006 |
| 2009/0192585 | A1 | 7/2009 | Bloom et al. | WO | 2008/047354 | 4/2008 |
| 2009/0192586 | A1 | 7/2009 | Tabor et al. | WO | 2008/100599 | 8/2008 |
| 2009/0192591 | A1 | 7/2009 | Ryan et al. | WO | 2008/138584 | 11/2008 |
| 2009/0198316 | A1 | 8/2009 | Laske et al. | WO | 2008/150529 | 12/2008 |
| 2009/0216310 | A1 | 8/2009 | Straubinger et al. | WO | 2009/002548 | 12/2008 |
| 2009/0216312 | A1 | 8/2009 | Straubinger et al. | WO | 2009/029199 | 3/2009 |
| 2009/0216313 | A1 | 8/2009 | Straubinger et al. | WO | 2009/042196 | 4/2009 |
| 2009/0234443 | A1 | 9/2009 | Ottma et al. | WO | 2009/045338 | 4/2009 |
| 2009/0240264 | A1 | 9/2009 | Tuval et al. | WO | 2009/061389 | 5/2009 |
| 2009/0240320 | A1 | 9/2009 | Tuval | WO | 2009/091509 | 7/2009 |
| 2009/0287296 | A1 | 11/2009 | Manasse | WO | 2009/111241 | 9/2009 |
| 2010/0094411 | A1 | 4/2010 | Tuval et al. | | | |
| 2010/0100167 | A1 | 4/2010 | Bortlein et al. | | | |
| 2010/0131054 | A1 | 5/2010 | Tuval et al. | | | |
| 2010/0137979 | A1 | 6/2010 | Tuval et al. | | | |
| 2010/0161045 | A1 | 6/2010 | Righini | | | |

FOREIGN PATENT DOCUMENTS

| | | |
|---|---|---|
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. Volume II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England). Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

\* cited by examiner

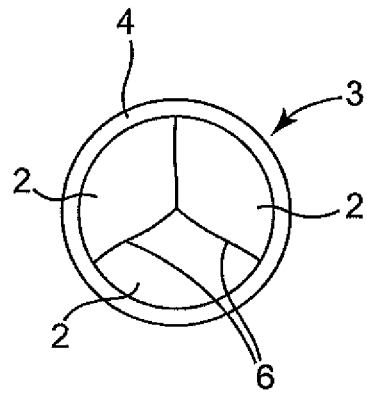
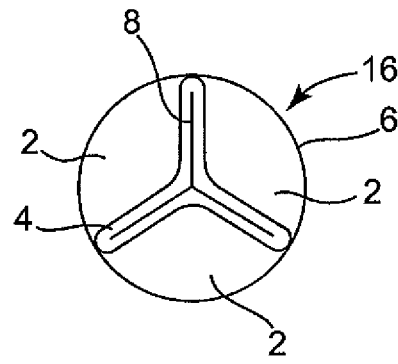
Fig. 1
Fig. 2
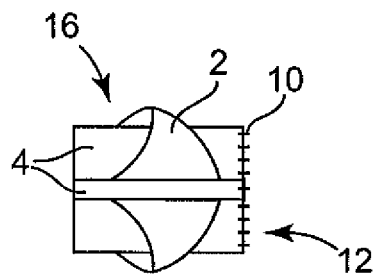
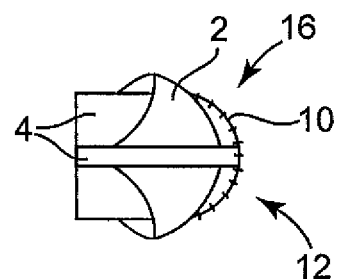
Fig. 3
Fig. 4
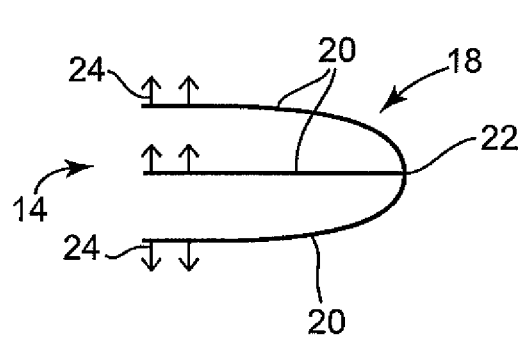
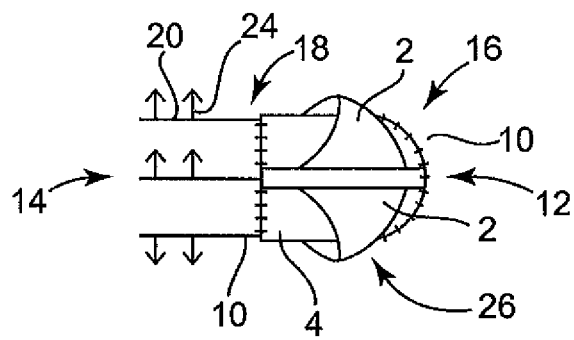
Fig. 5
Fig. 6

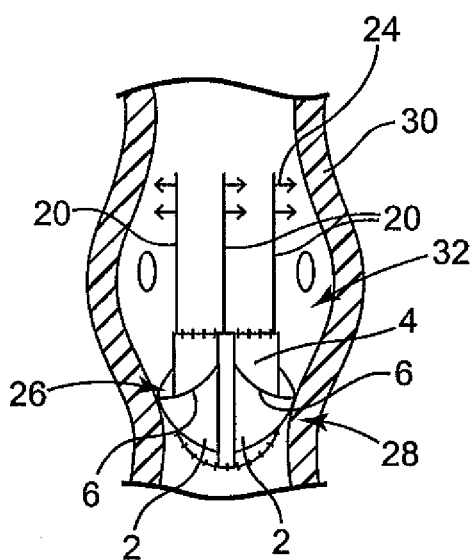
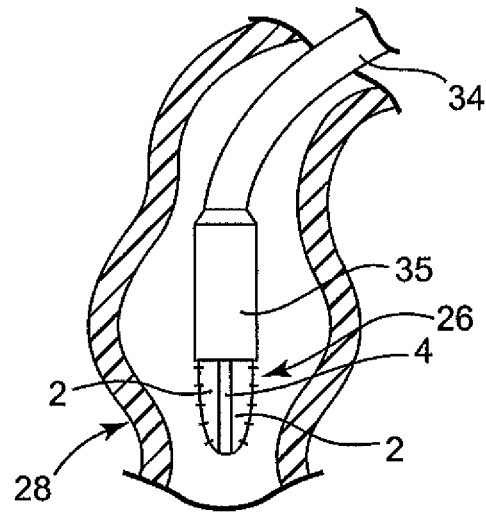
Fig. 7  Fig. 8
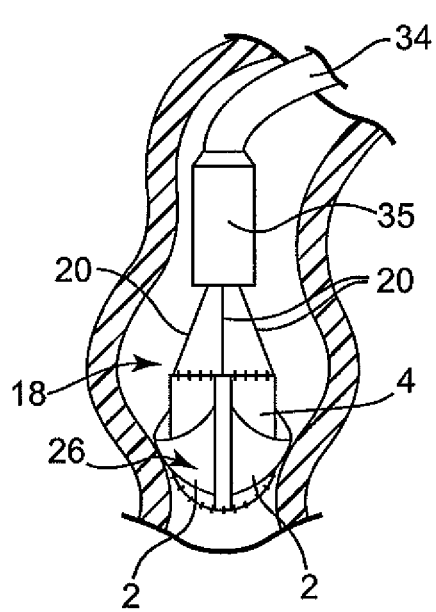
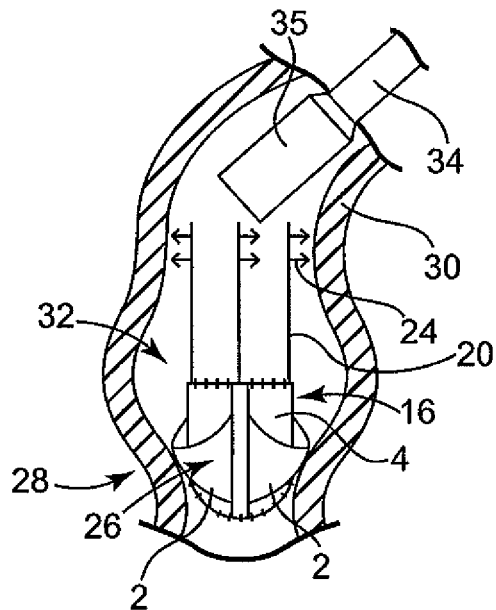
Fig. 9  Fig. 10

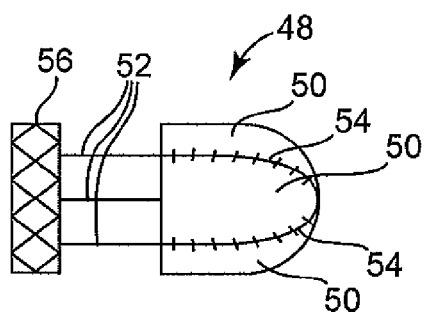
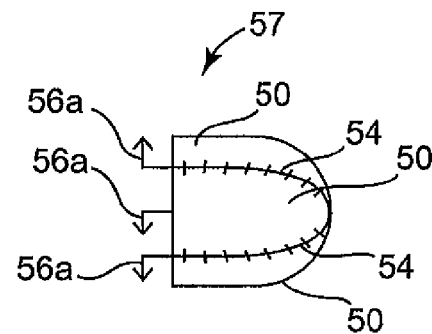
Fig. 15                Fig. 16
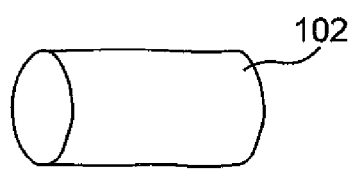
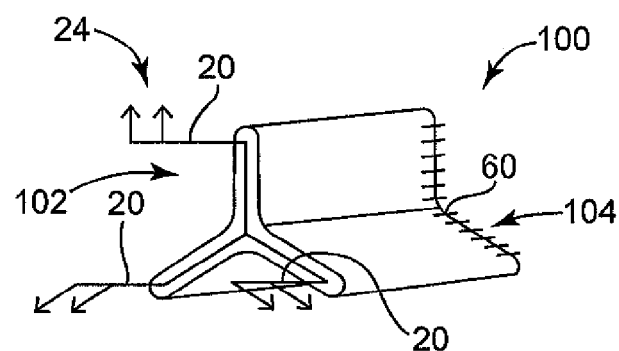
Fig. 17                Fig. 18
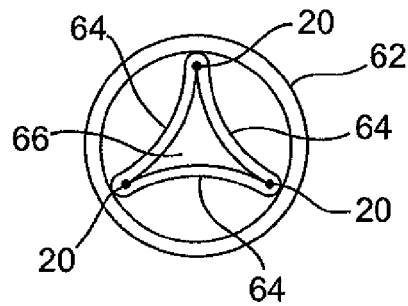
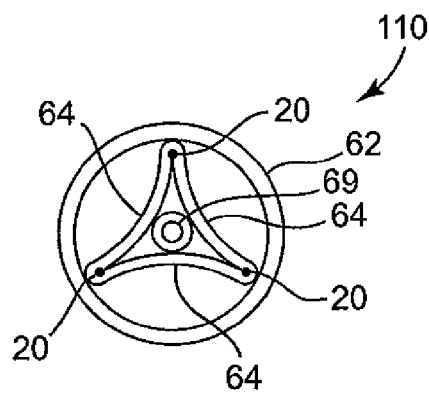
Fig. 19                Fig. 20

PROSTHETIC CARDIAC AND VENOUS VALVES

PRIORITY CLAIM

This application is a divisional application of U.S. application Ser. No. 11/527,769, filed Sep. 26, 2006, entitled "PROSTHETIC CARDIAC AND VENOUS VALVES," now abandoned, which claims the benefit of United States Provisional Patent Application having Ser. No. 60/720,398 filed on Sep. 26, 2005, entitled "Prosthetic Cardiac Valves", the entire disclosures of which are incorporated herein by reference for all purposes.

TECHNICAL FIELD

The present invention relates to prosthetic heart and venous valves used in the treatment of cardiac and venous valve disease. More particularly, it relates to minimally invasive and percutaneous replacement of cardiac and venous valves.

BACKGROUND

Recently, there has been a substantial level of interest in minimally invasive and percutaneous replacement of cardiac valves. In the specific context of pulmonary valve replacement, U.S. Patent Application Publication Nos. 2003/0199971 A1 and 2003/0199963 A1, (Tower et al.), which are incorporated herein by reference in their entireties, describe a valved segment of bovine jugular vein mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. The valve is also useful to replace failed pulmonary valves located in valved conduits.

U.S. Pat. No. 5,411,552 (Andersen et al) discloses a percutaneously deliverable valve for aortic valve replacement. Like the Tower et al. valve, this valve system employs a stent external to the valve to exert pressure against the vessel at the implant site to provide a seal. This pressure of the stent against the vessel also helps to keep the valve from becoming displaced once it has been implanted. With these and other percutaneously delivered valves, the stent or other expandable member is typically designed to surround at least the valve orifice. This basic configuration allows blood to flow through the center of the valve when the valve is open, with the multiple valve leaflets sealing against themselves to close the valve. Because the native aortic valve annulus in which the replacement is to be implanted may be calcified and have an irregular perimeter, this basic configuration can be problematic, particularly in the context of replacement aortic valves. For example, a valve annulus with an irregular perimeter can make it difficult for an expanded stent to accurately follow the contours of the native annulus, which can result in peripheral fluid leakage. This problem is typically not present in traditional surgically implanted valves, since their relatively rigid stents are typically sealed to the valve annulus with a sealing ring that is attached to the annulus by means of numerous sutures.

Other procedures and devices that have been developed include, for example, surgically implantable valves disclosed in U.S. Pat. Nos. 4,339,831 (Johnson) and 5,449,384 (Johnson), both of which are incorporated herein in their entireties. These valves have a configuration that is essentially the opposite of the natural configuration, such that the valve leaflets open inwardly and close by expanding outwardly to contact the native aortic valve annulus. These valves further include a framework comprising a plurality of struts that are sutured to the patient's annulus or an artificial annulus reconstruction ring and a flexible membrane attached to the framework to allow the membrane segments or leaflets to freely open inward to allow forward blood flow through the valve. Although the struts are described as being flexible, these valves are not contemplated to be implanted percutaneously due to the need to physically suture these implantable valves to the annulus of a patient. Another type of valve that was developed is described in U.S. Pat. No. 3,671,979 (Moulopoulos). This reference discloses a valve that can be inserted, withdrawn and retained relative to its desired implanted position with the use of a catheter. A membrane of the valve expands outward like an umbrella to seal against the interior of the aorta, downstream of a damaged aortic valve, and collapses and enfolds the catheter to allow flow of blood when the valve is open. However, this valve is not capable of being retained in this position and functioning as a valve without the use of its catheter.

There is a continued desire to provide cardiac valves that can be implanted in a minimally invasive and percutaneous manner, while minimizing or eliminating paravalvular leakage.

SUMMARY

The present invention is particularly directed to improvements in minimally invasive and percutaneously delivered valves for use in pulmonary and aortic positions. However, the invention may also be useful in other types of valves, including other heart valves and peripheral venous valves. In particular, a valve of the invention has leaflets that are configured to operate in an essentially an opposite manner from a typical artificial valve. Using this reverse or opposite configuration in a minimally invasively or percutaneously delivered valve with a collapsible stent can provide certain benefits. In particular, the outwardly sealing valve leaflets may adapt themselves or conform more readily to irregular configurations of the orifice in which the valve is mounted, thereby overcoming or reducing the sealing problems sometimes associated with expandable stents that are external to the valve leaflets.

The present invention also includes embodiments of a variety of outwardly sealing multi-leaflet valves, which are believed to be especially useful in conjunction with a number of different embodiments of collapsible stents.

In some embodiments of the invention, the valve leaflets are produced by inverting a section of a naturally valved vessel, such as a porcine aorta or a bovine jugular vein. In other embodiments, the valve leaflets are produced by sealing one end of a flexible tube and employing the unsealed end to define the leaflets. In yet other embodiments, the valve is produced by stitching together leaflets of flexible material such as pericardial tissue to provide a generally cup shaped structure. With any of these described embodiments, the valve leaflets are mounted to an expandable stent which is to be anchored to the orifice in which the valve is implanted. This valve implantation is positioned to be downstream of or adjacent to the free edges of the leaflets.

In some embodiments of the invention, the expandable stent may be configured with a flexible frame that is manufactured of a material consistent with being collapsed to allow delivery through a tubular percutaneous catheter or minimally invasive tubular surgical port type device. In other embodiments, the stent may include a self-expanding or balloon expandable circumferential stent that is located downstream of the free edges of the valve leaflets. In still other embodiments the stent may include outwardly extending barbs that are preferably, but not necessarily, located downstream of the free edges of the leaflets.

In one embodiment of the invention, a prosthetic heart or venous valve is provided, the valve comprising a central tissue structure comprising multiple tissue lobes extending from a common central area, wherein each of the lobes includes a longitudinal slot. The valve further comprises a plurality of leaflets extending from the central tissue structure and positioned between two adjacent lobes, wherein each of the leaflets comprises a free end spaced from the central tissue structure, and also comprises a compressible and expandable stent frame comprising a plurality of extending arms, wherein each of the extending arms of the stent frame is positioned at least partially within one of the longitudinal slots of the central tissue structure. The central tissue structure can comprise a native valve segment that has been inverted to provide the plurality of leaflets, wherein the multiple tissue lobes can be formed by folded portions of an aortic wall of the native valve segment.

In another aspect of the invention, a prosthetic valve is provided, which comprises a flexible tube having an inflow end and a outflow end, wherein the inflow end of the tube is folded against and attached to itself and the outflow end of the tube is unattached to itself, and a stent having multiple longitudinally extending members located at least partially within the tube and extending to the open outflow end of the tube, wherein portions of the tube that are adjacent the outflow end of the tube and between the longitudinally extending members of the stent are moveable toward and away from a central area of the valve to provide a plurality of valve leaflets.

BRIEF DESCRIPTION OF THE DRAWINGS

The present invention will be further explained with reference to the appended Figures, wherein like structure is referred to by like numerals throughout the several views, and wherein:

FIG. 1 is a top view of a natural aortic valve;

FIG. 2 is a top view of the natural aortic valve of FIG. 1 with the valve structure turned "inside-out" on itself such that the leaflets are positioned on the outside of the valve in a tri-lobed configuration;

FIG. 3 is a side view of the natural aortic valve turned "inside-out" as in FIG. 2, with the aortic wall sutured to itself at an inflow end of the valve;

FIG. 4 is a side view of the natural aortic valve turned "inside-out" as in FIG. 2, with the aortic wall sutured to itself at an inflow end of the valve, wherein the aortic wall is trimmed to more closely match the configuration of typical valve leaflets;

FIG. 5 is a side view of one embodiment of a stent for use in conjunction with valves of the type illustrated in FIGS. 3 and 4;

FIG. 6 is a side view of the stent of FIG. 5 mounted inside a valve of the type illustrated in FIG. 4 to provide one embodiment of a completed replacement valve of the invention;

FIG. 7 is a side view of the replacement valve of FIG. 6, as positioned within an aortic annulus, which is illustrated in cross-section;

FIG. 8 is a side view of a delivery catheter or device positioned within an aortic annulus, with the replacement valve of FIG. 6 partially advanced from one end of the catheter or device;

FIG. 9 is a side view of the delivery catheter or device illustrated in FIG. 8, with the replacement valve of FIG. 6 being further advanced from one end of the catheter into the aortic annulus;

FIG. 10 is a side view of the replacement valve of FIG. 6 in a desired position within an aortic annulus, which is also the position it will generally be in after it has been completely advanced from the end of the delivery device of FIGS. 8 and 9;

FIG. 15 is a side view of an alternative structure to provide valve leaflets that are mounted to a stent to provide an alternative embodiment of a completed replacement valve of the invention;

FIG. 16 is a side view of the alternative valve leaflet structure of FIG. 15, which uses an alternative stent configuration;

FIG. 17 is a side view of a flexible tube of natural or synthetic material as can be used for replacement valves of the invention;

FIG. 18 is a perspective view of a replacement valve fabricated from the tube of FIG. 17 and mounted to a stent, which includes having its inflow end sutured to produce a tri-lobed structure;

FIG. 19 is a top view of the replacement valve of FIG. 18, as located within the aortic annulus;

FIG. 20 is a top view of an alternative structure of the replacement valve of FIG. 18;

DETAILED DESCRIPTION

Figure 11:
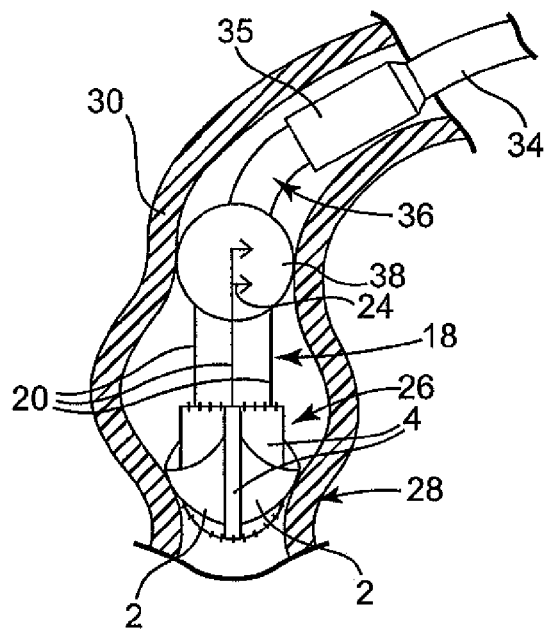
FIG. 11 is a side view of a delivery catheter within an aortic annulus that includes a balloon catheter that is radially expandable to anchor a replacement valve into the tissue of a patient.

Referring now to the Figures, wherein the components are labeled with like numerals throughout the several Figures, and initially to FIG. 1, a natural aortic valve 3 is illustrated, which generally comprises three leaflets 2 extending from an aortic wall 4. The leaflets 2 meet at their free edges 6 to seal the valve orifice when the valve 3 is in its closed position. The free edges 6 can move away from each other and toward the aortic wall 4, however, when the valve 3 is in its open configuration, thereby creating an open passage for blood flow. Such a natural aortic valve 3 may be a valved segment of a porcine valve, for example, which can be particularly advantageous in certain aspects of the invention due to the relatively thin aortic walls of these valves.

FIG. 2 illustrates an top view of an aortic valve 16, which is basically the valve 3 of FIG. 1 turned "inside-out" as compared to its natural state. That is, the aortic wall 4 is folded or rolled inwardly so that the side of the wall 4 that was previously facing in an outward direction is on the inside of the valve 16. The aortic wall 4 is further configured so that it defines a tri-lobed configuration, with the leaflets 2 on the outside of the valve 16 rather than the inside of the valve, as will be described in further detail below. In this configuration, the free edges 6 of leaflets 2 are located at the external periphery of the valve 16 such that the free edges 6 no longer will be in contact with each other when the valve 16 is in its closed configuration, but instead will be in contact with the vessel in which it is implanted (e.g., aorta). In fact, the leaflets 2 are facing in a generally opposite direction from the direction they are facing in a valve in its natural state.

In the embodiment of FIG. 2, the aortic wall 4 further defines three internal longitudinally extending slots 8 in the area where the wall 4 is folded onto or toward itself. That is, each of the lobes of the tri-lobed configuration includes a slot 8 extending through it. Because the valve 16 opens inwardly, rather than outwardly, relative to the structure in which it is positioned (e.g., an aorta), the leaflets 2 will seal against the aorta or other structure in which the valve is positioned when the valve 16 is in a closed state and will move toward the inner, tri-lobed structure when the valve 16 is in an open state. Thus, paravalvular leakage can be minimized or eliminated as compared to valves in which the radial strength of a stent is an issue.

In order to allow the free edges 6 of leaflets 2 of FIG. 2 to better conform to the tissue annulus in which the valve 16 is positioned, it is desirable for the leaflets 2 to have a certain level of elasticity. This can be accomplished by fixing the valve material with glutaraldehyde, for example, using conventional high, low or zero pressure fixation techniques, although other fixing techniques and materials can be used. In some embodiments, the aortic wall 4 may be trimmed to reduce the thickness of the wall, which will provide different properties for the valve (e.g., strength, flexibility, and the like). In addition to the porcine valve material discussed above, such a valve structure can be produced, for example, starting with a valved segment of bovine jugular vein that is trimmed to make its walls thinner and thus more adaptable to at least some of the valve configurations of the invention.

FIG. 3 illustrates a side view of the valve 16 of FIG. 2, with adjacent portions of an inflow end 12 of the folded aortic wall 4 attached to each other by sutures 10 to seal the end of the valve 16 and maintain the tri-lobed structure. Alternatively, adhesive or other surgical fasteners can be used to secure the inflow end 12 of the structure in such a configuration. In either case, in order to pull the sections of the wall 4 closer to each other along the slots 8, a vacuum can be pulled on the valve 16 prior to using the sutures or other material to seal the end of the valve 16. FIG. 4 illustrates an alternative embodiment of the aortic valve of FIG. 3, with the inflow end 12 of the aortic wall 4 being trimmed into a curved shape to more closely match the configuration of the bases of the valve leaflets 2 and to eliminate excess valve material extending beyond the leaflets 2.

Referring now to FIG. 5, one embodiment of a stent 18 is shown, which can be used in conjunction with valves of the type illustrated in FIGS. 3 and 4. The stent 18 includes three longitudinally extending curved arms 20 that extend from a common point 22, which will be positioned adjacent to the inflow end of a replacement valve. The arms 20 are shown as being generally the same length as each other in this figure, which will be adaptable to the implantation location of most replacement valves. It is possible, however, that at least one of the arms 20 is a different length than the other arms 20, such as in cases where particular anatomical needs of a patient need to be accommodated, when certain anchoring techniques are used, or when other considerations of the patient, the valve, or the delivery systems need to be considered, for example. The three arms 20 can be angularly displaced approximately 120 degrees from one another so that they are evenly spaced around the perimeter of the stent 18; however, it may instead be desirable to position the arms 20 at different angular spacings from each other.

In one embodiment of the invention, one or more of the arms 20 further include outwardly extending barbs or connectors 24 at an outflow end 14 of the stent 18. These connectors 24 are designed to engage with the wall of the aorta or other tissue structure in which the stent 18 may be positioned. Connectors 24 can include a wide variety of configurations and features, such as the arrow-shaped tips shown, or other configurations that provide for engagement with tissue through a piercing or other similar motion, and further do not allow the connector to disengage from the tissue with normal movement of the stent within the tissue. Each of the arms 20 of this embodiment are shown as including two barb-like connectors 24; however, more or less than two connectors 24 may extend from a single arm 20, and each of the arms 20 of a stent 18 may include the same or a different number of connectors 24.

The stent 18 is constructed of a material that is sufficiently flexible that it can be collapsed for percutaneous insertion into a patient. The material is also preferably self-expanding (e.g., Nitinol) such that it can be readily compressed and re-expanded. The material should further be chosen so that when the stent 18 is positioned within an aorta, for example, it exerts sufficient pressure against the aortic walls that fluids cannot leak past the stent 18. In particular, the stent 18 should provide enough radial outward force so that the tips or ends of the fold material of a tri-lobed structure can press against the inside walls of an aorta or other structure of a patient in such a way that blood cannot flow past these tips of the replacement valve. In this and any of the embodiments of the invention, the replacement valves and associated stents can be provided in a variety of sizes to accommodate the size requirements of different patients.

FIG. 6 illustrates the stent 18 of FIG. 5 mounted inside a valve 16 of the type illustrated in FIG. 4 to provide a completed replacement valve 26. As shown, the ends of the arms 20 extend beyond the ends of the valve 16 at the outflow end 14 of the valve; therefore, an area of the stent 18 relatively near the common point 22 (not visible in this figure) is positioned adjacent to the inflow end 12 of the valve 26. The adjacent tissue portions of the lobes at both the inflow end 12 and the outflow end 14 of the replacement valve 26 can be sewed or otherwise connected to each other, such as by sutures 10, in order to prevent or minimize the possibility of blood entering the slots 8 (see FIG. 2) of the tri-lobed structure.

The stent 18 is preferably retained in position within the slots 8 of aortic wall 4 by means of adhesive, sutures or other surgical fasteners. In one exemplary construction, the stent 18 is positioned within the slots 8 before the tissue is sutured or attached to itself at one or both of the inflow and outflow ends 12, 14. When the tissue at the inflow end 12 is sutured, the adjacent stent 18 can be sutured to the valve 26 at the same time, such that one stitching operation can serve the dual purpose of sealing the inflow end 12 of the valve 26 and also securing the stent 18 to the valve 26.

Referring now to FIG. 7, a replacement valve of the type generally shown as the valve 26 in FIG. 6 is illustrated, as mounted in an aortic annulus 28 of a patient. The valve 26 is positioned so that the free edges 6 of the leaflets 2 contact the annulus 28 around at least a substantial portion of the circumference of the aortic annulus 28, and preferably contact the annulus 28 around its entire circumference. The valve 26 is further positioned along the length of the aorta so that the connectors 24 are above the sinuses of Valsalva 32 and adjacent to a wall 30 of the patient's aorta. The connectors 24 are shown here as being slightly spaced from the wall 30, such as when the valve 26 is in an at least slightly compressed or unexpanded state. However, the arms 20 will be move or be forced to move at least slightly outward toward the walls 30 until the connectors 24 are imbedded or engaged with at least a portion of the thickness of the walls 30. These connectors 24 will then serve the purpose of retaining the valve 26 in its desired implant location relative to the aorta. In one embodiment, the connectors 24 can be designed to extend through the entire thickness of the walls 30 such that they will basically be anchored to the outside surface of the aortic walls 30. Alternatively, the connectors may be designed to extend only through a portion of the thickness of the walls 30, which, in order to keep the valve 26 securely in place, may require a different style of connector than a connector that extends entirely through an aortic wall. That is, connectors that need to engage within the thickness of a tissue can include a number of barbs or tissue engaging structures on each connector, while a connector that extends all the way through the tissue may only need to have a relatively wide base that will not easily pass backward through the hole it created when originally passing through the tissue.

In order to prevent possible interference between the patient's native valve and a replacement valve of the type illustrated in FIG. 6, for example, the native valve can be completely or partially removed. In some cases, the native valve may be left in its original location; however, the replacement valve in such a circumstance should be positioned in such a way that the remaining native valve does not interfere with its operation. In cases where the native valve is to be removed, exemplary valve removal or resection devices that can be used are described, for example, in PCT Publication WO/0308809A2, which is incorporated herein by reference in its entirety.

FIGS. 8-10 illustrate an end portion of one exemplary delivery device and exemplary sequential steps for using such a device for delivering a replacement valve 26 to 30 its desired location within a patient. In particular, FIG. 8 illustrates a tubular delivery device 34 that has been advanced to the general location where the replacement valve 26 will be implanted. In order to reach this location, the delivery device 34 is inserted into the body using one of a number of different approaches. For example, the device 34 can reach the aorta through a retrograde approach originating at a location distal to the heart, such as the femoral artery. Alternatively, an antegrade approach could be used, which originates at a location distal to the heart, such as the femoral vein or an incision in the ventrical wall or apex. In any case, the device 34 is moved to the desired implantation area of the body with a replacement valve 26 being partially or entirely enclosed within an outer sheath 35. As shown in the figure, the portion of sheath 35 at the distal end of device 34 is at least slightly larger in diameter than the adjacent portion of the device 34, which will help to keep the valve 26 positioned near the distal end of device 34 (i.e., keep it from translating along the length of the device 34). However, the distal end of the sheath 35 may additionally or alternatively include a stop or some other configuration that keeps the valve 26 from migrating away from the distal end of device 34.

With particular reference to FIG. 8, the replacement valve 26 is shown as it is beginning to be advanced out of the end of a tubular delivery device 34 by pulling back the sheath 35, thereby releasing or exposing one end of the replacement valve 26. In accordance with the invention, the valve 26 is delivered in a radially compressed configuration to ease passage of the device 34 through the vascular system; however, the valve 26 will be able to expand after it is released from the end of the device 34. The leaflets 2 of the valve 26 are first are advanced distally out of the end of the device 34, as illustrated in FIG. 8, so that they can be properly located relative to the aortic annulus 28. FIG. 9 illustrates the replacement valve 26 as it is further released from the device 34 by further retraction of the sheath 35. As the delivery device 34 is withdrawn, the stent 18 of the valve 26 is allowed to expand and seat the replacement valve 26 in its desired location.

Finally, FIG. 10 illustrates the stent of the replacement valve 26 after the delivery device 34 has been retracted a sufficient amount that it is completely separated from the valve 26. In this embodiment, the arms 20 are configured so that they tend to expand radially outwardly once they are released from the sheath 35. The outward radial force causes the barbs or connectors 24 to embed or otherwise engage with the wall 30 of the patient's aorta to anchor the replacement valve 26.

Although the arms 20 are shown as relatively straight wires in the embodiment of the replacement valve 26 described above, the stents of the invention may be shaped and/or positioned differently than previously described. For one example, the stent arms could instead be curved outwardly (i.e., convex) to conform at least somewhat to the location of the body in which it will be positioned (e.g., aorta for aortic valve, pulmonary trunk for the pulmonic vein, vein for venous valve, and ventricle of mitral/tricuspid valve). This outward curvature of the stent arms can help to secure or anchor the valve in place and thus can have different degrees or amounts of curvature depending on the configuration of the particular replacement valve. Further, the barbs or connectors that extend from the stent arms can be positioned near the distal ends of the arms (i.e., spaced relatively far from the valve, such as valve 16), as shown and described above, in order for these connectors to be positioned beyond the sinuses of Valsalva of the aortic valve of a patient. However, the barbs or connectors could alternatively or additionally be located closer to the valve, such as valve 16, which would position the connectors closer to the outflow end of the replacement valve.

FIG. 11 illustrates an optional additional use of a balloon catheter 36 on the delivery device 34 to help to anchor the valve 26 in place in the aorta or other tissue of a patient. In particular, balloon catheter 36 includes a balloon 38, which is located radially between the arms 20 of the stent 18 when the sheath 35 has been retracted from the valve 26. During the process of inserting the device 34 into the patient, balloon 38 will generally be at least partially deflated in order to minimize its size and allow for easier percutaneous insertion of the valve 26. Once the valve 26 is in its desired location relative to the walls 30 with which it will be engaged, the balloon 38 is inflated via the balloon catheter 36. The inflation of balloon 38 can be carefully monitored, such as by measuring pressures of forces, to expand the arms 20 outwardly by a particular amount, thereby driving the barbs or connectors 24 toward and into the wall 30 of the patient's aorta.

While the procedure illustrated in FIGS. 8-11 illustrates placement in the aortic annulus using a percutaneous catheter to deliver the valve retrograde to blood flow, antegrade delivery of the valve is also within the scope of the invention. Similarly, while delivery using a catheter is illustrated, the valve could alternatively be compressed radially and delivered in a minimally invasive fashion using a tubular surgical trocar or port. In addition, as noted above and as will be discussed further below, the valve may be delivered to sites other than the aortic annulus.

Figure 12:
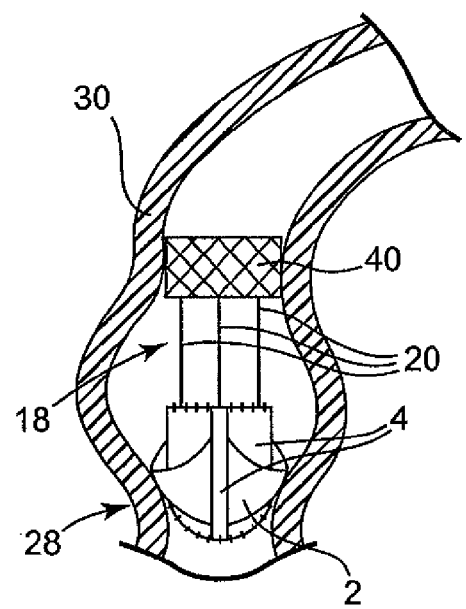
FIG. 12 is a side view of an alternative embodiment of a replacement valve of the type illustrated in FIG. 6 as positioned within an aortic annulus, which includes an alternative embodiment for anchoring the valve.
Figure 13:
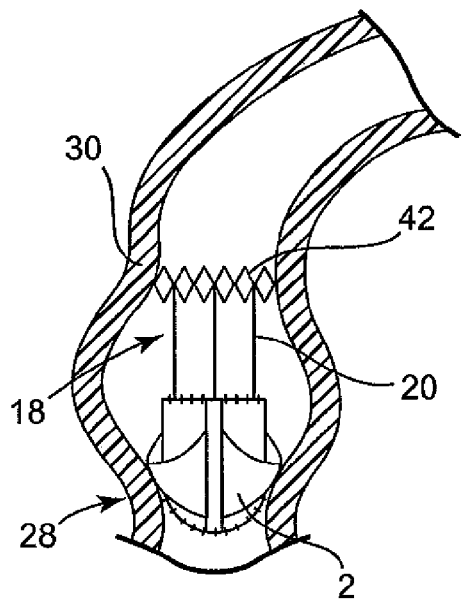
FIG. 13 is a side view of another alternative embodiment of a replacement valve of the type illustrated in FIG. 6 as positioned within an aortic annulus, which includes another alternative embodiment for anchoring the valve.

FIGS. 12 and 13 illustrate alternative replacement valves that are similar in structure to the valve 26 discussed above, but include alternative structures for anchoring the replacement valve. These replacement valves are again shown in the general location in which they will be positioned within an aortic annulus 28 of a patient. FIG. 12 illustrates a replacement valve that includes the stent 18 having multiple arms 20, but instead of these arms 20 including barbs or connectors, the arms 20 are stent wires that are coupled to a slotted-tube type stent ring 40. As is described above relative to another embodiment, the arms 20 of this embodiment may also be curved outwardly to conform at least somewhat to the location of the body in which it will be positioned. This outward curvature of the stent arms can help to secure or anchor the valve in place. Delivery of this valve can be performed using a procedure that is similar to that described above relative to FIGS. 8-11, or a different method can be used. Alternatively or additionally, some type of adhesive may be applied to the stent ring or a biocompatible covering (e.g., fabric, tissue, polymer, and the like) to help to keep the stent in place. In any case, stent ring 40 may be self-expanding or may be expanded by a balloon or other device that can radially expand the ring 40.

FIG. 13 illustrates a replacement valve that again includes the stent 18 having multiple arms 20. In this embodiment, the arms 20 are coupled to a stent 42 that is formed of one or more zig-zag wires. The wires are arranged relative to each other in such a way that they provide sufficient radial strength to keep the valve in place relative to the aortic annulus 28 or other location to which the valve is delivered. Again, delivery of this valve can be performed using a procedure that is similar to that described above relative to FIGS. 8-11, or a different method can be used. In any case, stent 42 may be self-expanding or may be expanded by a balloon or other device that can radially expand the stent 42.

Figure 14:
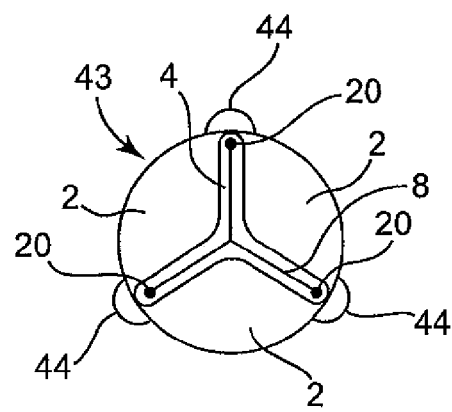
FIG. 14 is a top view of a replacement valve generally of the type illustrated in FIG. 6, which further includes optional tissue or fabric portions to prevent leakage adjacent the valve commissures.

FIG. 14 illustrates another embodiment of the replacement valve 26 of FIG. 6. In particular, a replacement valve 43 is shown, which includes the same basic structure of the aortic valve 3 of FIG. 2, and further including the stent 18 including arms 20, as in FIG. 5. The tips of the arms 20 of stent 18 are located in the slots 8 and are visible in this top view of the valve 43. The valve 43 further includes optional bulbous portions 44 that extend from each of the tips of the lobes of the tri-lobed structure of the valve 43. These portions 44 are provided to further insure secure contact between the valve 43 and the aorta or other structure in the areas adjacent to the leaflets 2, thereby further minimizing or preventing leakage adjacent the valve commissures. These portions 44 may be made of a tissue, fabric, or other material, as desired.

FIG. 15 illustrates a replacement valve 48, which includes an alternative structure to provide valve leaflets. In this embodiment, leaflets 50 are cut or otherwise formed from Pa natural or synthetic flexible material (e.g., pericardial tissue, polymeric material, fabric, and the like), and are attached to multiple arms 52 of a stent via sutures, glue, or some other attachment material or method. The leaflets 50 are further attached to one another by means of sutures 54 to define a generally cup-shaped structure. The valve leaflets 50 comprise the regions of the cup-shaped structure located between the longitudinally extending arms 52 of the stent. The arms 52 of the stent can correspond generally to the arms 20 of the stent of FIG. 5, or can be arranged and configured differently. The stent and leaflets could also be constructed together using processes and materials disclosed, for example, in U.S. Pat. Nos. 6,458,153; 6,652,578; and 7,018,408 (all to Bailey et al.), which are incorporated herein by reference. In this embodiment of FIG. 15, the arms 52 are coupled to an expandable slotted tube type stent 56, which may be self-expanding or balloon-expandable similar to the stent 40 of FIG. 12. Other forms of circumferential stents, barbs, or other structures may be used in addition to or as an alternative to the slotted tube type stent structure 56 shown in this figure. Delivery of the valve can correspond generally to the procedure described above relative to FIGS. 8-11, although other delivery devices and methods can be used.

FIG. 16 illustrates another embodiment of a replacement valve 57, which uses the valve leaflet structure of FIG. 15 with a different anchoring embodiment in place of the stent 56. In particular, replacement valve 57 includes stent arms 56a that correspond generally to those of the stent 18 described above, but do not extend as far past the outflow end of the replacement valve as the stent arms of the replacement valve 26 of FIG. 6. Because the valve leaflets 50 of this embodiment present an essentially planar circular free edge, the stent may be anchored to tissue closely adjacent the aortic valve annulus. Barbs, connectors, and/or various forms of circumferential stents may be used in combination with the stent arms 56a to anchor the replacement valve 57 in place. Delivery of the valve 57 can correspond generally to the procedure described above relative to FIGS. 8-11, although other delivery devices and methods can be used.

In the embodiments of FIGS. 15 and 16 described above, the stent arms are illustrated as being positioned in the interior portion of the cup-shaped structure; however, the arms could alternatively be positioned and attached on the outside of the cup-shaped structure. Attachment of the stent to the valve structure could be accomplished by suturing, perforating the wire through the leaflets, adhering, welding, and the like. In any of these embodiments, the method used to attach the leaflets to each other in a cup-shaped structure may be the same or different than the method used to attach a stent either to the inside or outside of this cup-shaped structure FIG. 18 illustrates another embodiment of a replacement valve 100, which can be fabricated from a piece of flexible tubing, such as is shown in FIG. 17 as a flexible tube 102. Flexible tube 102 may be a natural or synthetic material, such as pericardial tissue, for example (which is discussed, for example, in U.S. Pat. No. 5,482,424, the contents of which are incorporated herein by reference). Replacement valve 100 utilized the flexible tube 102, which is sutured to itself by sutures 60 at an inflow end 104, although other attachment methods may additionally or alternatively be used, such as adhesive or other surgical fasteners. The attachment of the tube 102 to itself produces a tri-lobed structure much like that of the inflow end of the aortic wall 4 of the replacement valve 26 of FIG. 6. However, in this embodiment, the flexible tube 102 is not sutured or attached to itself at an outflow end 106.

The valve 100 further includes a stent that is similar to the stent 18 illustrated in FIGS. 5 and 6, which includes multiple extending arms 20. In this embodiment, the tube 102 is mounted so that the arms 20 extend through slots in the tri-lobed structure and can be attached thereto by sutures, adhesives or other means. However, other stent configurations can also be used, such as using three separate straight wires in substitution for arms 20, which wires can be mounted within the lobes of the tube 102 in its tri-lobed configuration. In any case, the arms 20 or other stent structures can include barbs or connectors 24 for attachment to the walls of an aortic annulus or other tissue structure. As with other embodiments of replacement valve attachment discussed above, self-expanding or balloon expandable stents may alternatively or additionally be attached to or extend from arms 20 for attachment to tissue of a patient.

In this embodiment of a replacement valve 100, the outflow end 106 is not sealed to itself, allowing the downstream portion of the tube located between the arms 20 of the stent 18 to serve as the leaflets of the valve. That is, the replacement valve 100 is illustrated in FIG. 18 in its open position, where blood can flow past the outer surfaces of the valve from the inflow end 104 toward the outflow end 106. Delivery of the valve corresponds to the procedure illustrated in FIGS. 8-11. When the replacement valve 100 is in its closed, position, the outflow end 106 essentially flares outwardly toward the walls of the aorta or other structure in which it is positioned, as will be discussed in further detail below.

FIG. 19 is a top view of the replacement valve 100 of FIG. 18, as located within a patient's aortic annulus 62. In this view it can be seen that the free end of the tube, in conjunction with the arms 20 of the stent 18, define three leaflets 64. In order for the leaflets 64 to properly close, it is desirable to have an entry point for backflow of blood to enter the interior of the tube to expand the leaflets 64. For this reason, the stent and leaflets of this embodiment can be sized so that a small central opening 66 remains open to the interior of the tube, even when the valve is open as illustrated. The same construction may be applied to valves 48 and 57 described above and illustrated in FIGS. 15 and 16.

Figure 21:
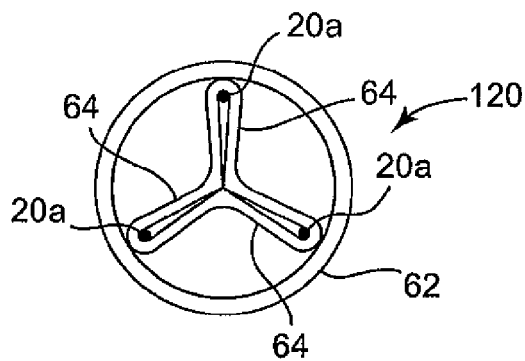
FIG. 21 is at top view of another alternative structure of the replacement valve of FIG. 18.
Figure 22:
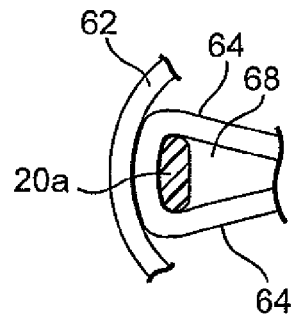
FIG. 22 is an enlarged top view of a portion of the replacement valve of FIG. 21.

FIGS. 20-22 illustrate additional exemplary embodiments of the replacement valve of FIGS. 18 and 19. In particular, FIG. 20 is a top view of a replacement valve 110 that allows for fluid entry into the interior of the tube facilitated by a small cylindrical or conical lumen 69, which is mounted in the interior portion of the stent. Lumen 69 acts as a type of a spacer to keep the leaflets 64 freely moveable relative to each other, thereby facilitating closing of the valve 110 with sufficient pressure from blood flow. That is, when the blood flow moves in a "backward direction relative to the pumping blood flow, it should move the leaflets 64 apart from each other and toward the aortic annulus or other structure in which it is positioned, thereby closing the valve 110.

FIG. 21 is a top view of a replacement valve 120 that allows for fluid entry into the interior portion of the tube at the commissures of leaflets 64 to facilitate closing of the valve 120. Small openings between the lobes of the structure are provided by means of enlarged segments on the arms 20a of the stent. FIG. 22 illustrates an enlarged detail of a portion of the embodiment of FIG. 21. In this view, an enlarged cross section portion of arm 20a of the stent and the associated small opening 68 are visible. All of these alternative constructions of FIGS. 20-22 may be applied to valves 48 and 57 described above and illustrated in FIGS. 15 and 16, along with other valves. Other structures may be used in addition to or instead of the devices of FIGS. 19-22, any of which should facilitate the closing of the valve.

Figure 23:
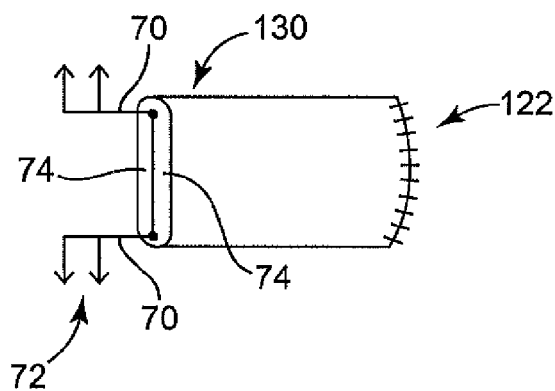
FIG. 23 is a perspective view of a replacement valve fabricated from the tube of the type illustrated in FIG. 17 and mounted to a stent, which includes having its inflow end sutured to create a bi-lobed structure.

FIG. 23 illustrates a replacement valve 130 that can be fabricated from the tube 102 of FIG. 17, for example. Valve 130 has its inflow end 122 sutured to itself to produce a flattened structure and is mounted to a stent. The stent may be a self-expanding stent taking the form of a u-shaped wire 70 having laterally extending barbs 72. The contours of the wires 70 can also be used to further secure the valve into its position within the patient. Alternatively, the stent may comprise two separate straight wires. The free end of the tube in conjunction with the stent defines two valve leaflets 74 which, when open, expand against the vessel or orifice in which the replacement valve is mounted. Delivery of the valve corresponds to the procedure illustrated in FIGS. 8-11, although other delivery devices and methods can instead be used.

Figure 24:
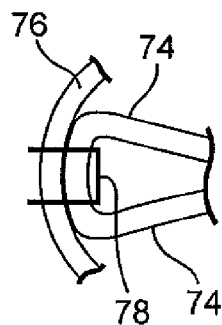
FIG. 24 is an enlarged top view of a portion of the replacement valve of FIG. 23.

FIG. 24 illustrates a detail of the replacement valve 130 of FIG. 23. As with the valve of FIG. 18, an inflow opening into the interior of the valve may be desirable to facilitate separation of the valve portions from each other to close the valve 130. In some embodiments, this might be provided by enlarged cross section portions of the wire 70. In alternative embodiments in which the free edges of leaflets are attached directly to a valve orifice 76, a simple staple 78 may be substituted, also providing an opening into the valve 130. Staple 78 may be attached to the stent and may self expand into the tissue of the annulus or may be balloon expanded, for example.

Figure 25:
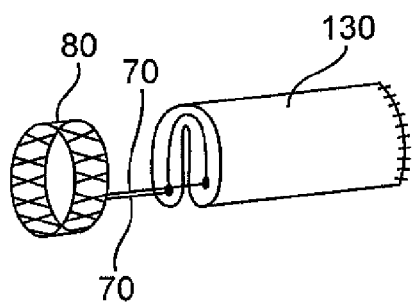
FIG. 25 is a perspective view of an alternative embodiment of the replacement valve of FIG. 23, which is folded onto itself to provide for passage through a catheter.

FIG. 25 illustrates the replacement valve 130 of FIG. 23, which is folded to allow passage through a catheter or other tubular delivery device. In this embodiment, the u-shaped stent wire 70 or other stent configuration is coupled to an expandable stent 80. By folding the replacement valve 130 rather than circumferentially compressing it, stress on the valve 130 is reduced.

Figure 26:
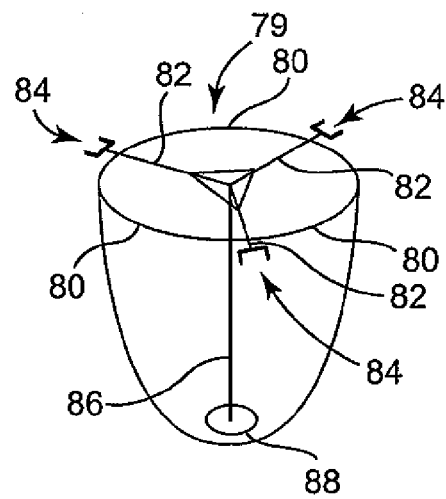
FIG. 26 is a perspective view of an alternative stent configuration for use with the leaflets configured in accordance with the present invention.

FIG. 26 illustrates an alternative stent configuration 79 for use with the leaflets of the above FIGS. 15-24. In this design, rather than employing multiple curved, longitudinally extending arms or wires, a single longitudinally extending wire 86 is used. Wire 86 includes an enlarged base 88 against which the inflow end of the valve leaflets rest. The commissures and thus the valve leaflets 80 are defined by two or three laterally extending wires 82, which are attached to the edges of the valve leaflets 80. The laterally extending wires 82 are provided with barbs or connectors 84 which anchor the replacement valve in place within the vessel or orifice in which it is implanted.

Figure 27:
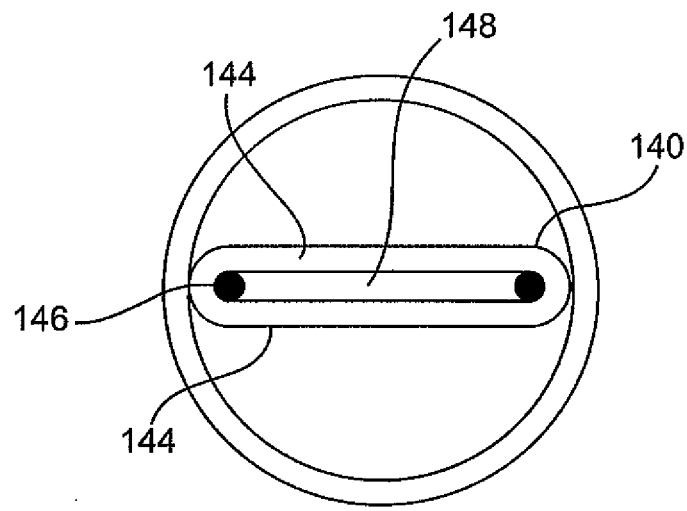
FIG. 27 is a top view of another embodiment of a replacement valve having a bi-lobed structure.
Figure 28:
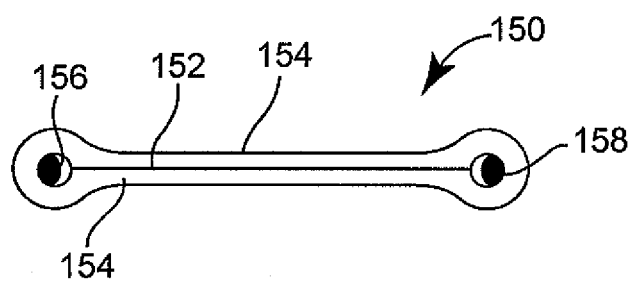
FIG. 28 is a top view of another embodiment of a replacement valve having a bi-lobed structure.

FIGS. 27 and 28 illustrate additional features that can be used with a replacement valve of the type described relative to valve 130. In particular, a replacement valve 140 is formed from a tube of material to create a bicuspid valve structure, as in FIG. 23. The valve has its inflow end sutured to itself to produce a flattened structure with a central longitudinal opening 148 in which a stent 146 is positioned. Again, the stent 146 may take the shape of a u-shaped wire with laterally extending barbs or connectors, or another stent configuration can be used. In any case, the stent 146 of this embodiment works in conjunction with the size of the slot 148 to provide at least a slight gap between the opposing leaflets 144. The slot 148 helps to facilitate opening of the leaflets 144 when the blood flows from the outflow end of the valve toward the inflow end, thereby closing the valve 140.

FIG. 28 illustrates a replacement valve 150 that is similar to valve 140, except that valve 150 includes a slot 152 that is not particularly designed to include a space between opposing leaflets 154. In order to facilitate separation of the leaflets 154, this valve 150 includes pockets 156 at both ends, which can be formed by the ends 158 of a stent positioned therein. For example, these ends 158 may be enlarged relative to the stent wire so that the stent can operate in its normal manner while the enlarged ends operate to form the pockets 156.

While a number of the valves described above are shown as having fixation barbs located downstream of the free edges of the valve leaflets, this need not necessarily be so. In fact, the planar, generally circular configuration of the free edges of the valve leaflets in the closed position would in some cases allow the barbs or connectors to extend outward through or adjacent to the free edges of the valves. Further, while the discussion of the valves above focuses mainly on placement in the aortic annulus, the valves may be employed in other locations including replacement of other heart valves and peripheral venous valves. Finally, while the valves as disclosed are described mainly in the context of percutaneously or minimally invasively delivered valves, they could also be placed surgically.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

The invention claimed is:

1. A prosthetic valve, comprising:
    a flexible tube comprising an inflow end, an outflow end, multiple lobes formed at the inflow end by attachment of the flexible tube to itself, and a central aperture at the outflow end of the tube,
    wherein each lobe includes a radial tip, the radial tip extending axially to the outflow end of the flexible tube; and
    a stent having multiple longitudinally extending members, each of which is located at least partially within one of the lobes of the tube and extending at least to the outflow end of the tube,
    wherein portions of the tube between each two adjacent longitudinally extending members of the stent are moveable toward and away from the central aperture to provide a plurality of valve leaflets,
    wherein the valve leaflets are biased toward the central aperture when the valve is in an open position during which fluid can flow from the inflow end to the outflow end of the tube,
    wherein the central aperture is open to the inside of the tube at the outflow end of the tube both when the valve is in its open position and when the valve is in a closed position.

2. The valve of claim 1, wherein at least one of the extending members further comprises a distal portion that extends beyond the outflow end of the tube, and
    wherein the distal portion of the at least one extending member further comprises an anchoring mechanism.

3. The valve of claim 2, wherein the anchoring mechanism of the at least one of the extending members comprises at least one connector that is engageable with a thickness of tissue.

4. The valve of claim 2, wherein the anchoring mechanism comprises a compressible and expandable engagement structure.

5. The valve of claim 1, wherein the at least one spacer extends from the inflow end of the tube and extends generally along a central longitudinal axis of the tube.

6. The valve of claim 5, wherein the at least one spacer is attached to an interior portion of the stent.

7. The valve of claim 1, wherein the at least one spacer comprises a lumen.

8. The valve of claim 7, wherein the lumen is cylindrical.

9. The valve of claim 7, wherein the lumen is conical.

10. The valve of claim 1, wherein the stent comprises three longitudinally extending members, and
    wherein the portions of the tube between each two adjacent longitudinally extending members form three valve leaflets.

11. The valve of claim 1, wherein the stent comprises two longitudinally extending members and the valve comprises two leaflets.

12. A prosthetic valve, comprising:
    a flexible tube having an inflow end and an outflow end, wherein the inflow end of the tube is folded against and attached to itself along an inflow edge of the flexible tube to form a plurality of lobes, and the outflow end of the tube comprises a central aperture; and
    a stent having multiple longitudinally extending members, each of which is located at least partially within one of the lobes of the tube and extending at least to the outflow end of the tube,
    wherein portions of the tube that are adjacent to the outflow end of the tube and between each two adjacent longitudinally extending members of the stent are moveable toward and away from the central aperture to provide a plurality of valve leaflets,
    wherein the stent comprises a distal portion that extends beyond the outflow end of the tube, and
    wherein the central aperture is open to the inside of the tube at the outflow end of the tube when the valve is in an open position and when the valve is in a closed position.

13. The valve of claim 12, wherein the plurality of lobes form a tri-lobed structure.

* * * * *